United States Patent [19]

Ziemkiewicz et al.

[11] Patent Number: 5,037,633

[45] Date of Patent: Aug. 6, 1991

[54] MICROBIOLOGICALLY STABILIZED PHASE FOR BICARBONATE TOOTHPASTE MANUFACTURE

[75] Inventors: Alexander G. Ziemkiewicz, Shelton; David R. Williams, Monroe, both of Conn.

[73] Assignee: Chesebrough-Pond's USA Co., division of Conopco, Inc., Greenwich, Conn.

[21] Appl. No.: 568,580

[22] Filed: Aug. 16, 1990

[51] Int. Cl.$^5$ .................. A61K 7/16; A61K 33/34
[52] U.S. Cl. .................................. 424/49; 424/630
[58] Field of Search ........................ 424/49–58, 424/630

[56] References Cited

U.S. PATENT DOCUMENTS

| 3,065,139 | 11/1962 | Ericsson et al. | 167/72 |
|---|---|---|---|
| 3,663,156 | 5/1972 | Meininger et al. | 8/601 |
| 3,681,492 | 8/1972 | Kotzbauer | 424/141 |
| 3,886,904 | 6/1975 | King | 119/3 |
| 3,937,804 | 2/1976 | Delaney et al. | 424/52 |
| 3,943,240 | 3/1976 | Delaney et al. | 424/49 |
| 3,962,417 | 6/1976 | Howell | 424/49 |
| 4,048,300 | 9/1977 | Tomlinson et al. | 424/49 |
| 4,160,022 | 7/1979 | Delaney et al. | 424/52 |
| 4,332,791 | 6/1982 | Raaf et al. | 424/52 |
| 4,375,421 | 3/1983 | Rubin et al. | 252/110 |
| 4,453,979 | 6/1984 | DeMasi et al. | 106/188 |
| 4,487,757 | 12/1984 | Kiozpeoplou | 424/7.1 |
| 4,528,180 | 7/1985 | Schaeffer | 424/52 |
| 4,687,663 | 8/1987 | Schaeffer | 424/52 |
| 4,840,808 | 6/1989 | Lee et al. | 426/270 |
| 4,849,213 | 7/1989 | Schaeffer | 424/53 |
| 4,853,213 | 8/1989 | Thame | 424/49 |
| 4,867,988 | 9/1989 | Chernack | 424/490 |

OTHER PUBLICATIONS

"Stabilisation, Disinfection, Preservation", Textbook edited by S. S. Block (1983), Chapter 11 by F. J. Turner, pp. 240–250.

*Primary Examiner*—Shep K. Rose
*Attorney, Agent, or Firm*—Milton L. Honig

[57] ABSTRACT

The invention provides a process for microbiologically stabilizing a premix phase intended to receive bicarbonate in the manufacture of toothpaste. The process includes blending together in the premix phase a polyol, a thickening agent, a copper compound and water. The premix phase is maintained at a temperature no higher than 110° F. for a time sufficient to destroy bacteria. Thereafter the bicarbonate is incorporated into the premix phase without cool-down of the premix phase. There is also disclosed an oral composition that includes a combination of humectant, thickening agent, copper, bicarbonate and water.

9 Claims, No Drawings

MICROBIOLOGICALLY STABILIZED PHASE FOR BICARBONATE TOOTHPASTE MANUFACTURE

BACKGROUND OF THE INVENTION

1. Field of the Invention

The invention relates to a process and composition for microbiologically stabilizing a toothpaste phase during the manufacture of a bicarbonate-containing toothpaste.

2. The Related Art

During normal toothpaste manufacture, it is common to form a "premix" of the liquid and water-soluble portions of the paste to facilitate semi-continuous production in the final product mixing tanks. To ensure microbiological stability, this premix phase is held at above 125° F. U.S. Pat. No. 4,453,979 (DeMasi et al) is typical of this art.

Baking soda (sodium bicarbonate) is a desirable toothpaste ingredient used as a mild abrasive. Unfortunately, this material cannot experience temperatures above 100° F. without undergoing decomposition. Therefore, it is necessary to cool any hot premix phase down to below 100° F. before combining baking soda therewith. This cool-down procedure is costly, time-consuming and adversely impacts plant output rates.

Accordingly, it is an object of the present invention to provide a means for microbiologically stabilizing a premix phase below 110° F. so that the phase can be combined without any prior cool-down with a bicarbonate component.

A further object of the present invention is production of a sodium bicarbonate toothpaste that can be formed in a semicontinuous process without using intervention of a cooling step during addition of the various components.

A still further object of the present invention is to provide a bicarbonate-containing finished dentifrice product that has been microbiologically stabilized.

These and other objects of the present invention will become more readily apparent upon consideration of the more detailed description and Examples which follow.

SUMMARY OF THE INVENTION

A process for the preparation of an oral composition is provided comprising:
  (i) blending together a premix phase whose components comprise:
    (a) a polyol present in an effective amount to operate as a humectant;
    (b) a thickening agent present in an effective amount to increase viscosity of said premix phase;
    (c) a copper compound present in an effective amount to inhibit growth of bacteria in said premix phase; and
    (d) the balance water;
  (ii) maintaining said premix phase at a temperature no higher than about 110° F. for a time sufficient to destroy bacteria in said premix phase; and
  (iii) combining from about 0.5 to about 80% by weight of a bicarbonate salt with said premix phase.

Another aspect of the present invention is provision of a microbiologically stabilized oral composition which comprises:

(a) a polyol present in an effective amount to operate as a humectant;
  (b) a thickening agent present in an effective amount to increase viscosity of said premix phase;
  (c) a copper compound present in an effective amount to inhibit growth of bacteria in said premix phase;
  (d) from about 0.5 to about 80% by weight of a bicarbonate salt; and
  (e) the balance water.

DETAILED DESCRIPTION

Production of bicarbonate based toothpaste has now been substantially improved by incorporation of a copper compound within the premix phase of the manufacture process. No longer is it necessary to hold the premix phase at temperatures above 110° F. to sterilize that phase and then cool the premix prior to the addition of bicarbonate to avoid thermal decomposition of the latter.

The premix phase will normally have three essential components. These components are a polyol, a thickening agent and water.

The polyols which serve as humectants may include glycerol, sorbitol, propylene glycol, lactitol, xylitol, polypropylene glycol, polyethylene glycol, hydrogenated corn syrup and mixtures thereof. Particularly preferred is a mixture of sorbitol and glycerol. Generally the amount of polyol will range from about 25 to 99.9% by weight, preferably from about 70 to 95% by weight of the premix phase. With respect to the finished bicarbonate product, the polyol will range in concentration from about 25 to 80% by weight.

The thickening agent employed in this invention will normally be present in an amount from 0.1 to 10%, preferably about 0.5 to 5% by weight of the premix phase. With respect to the finished product, the amount of thickening agent may range over a similar concentration. Thickeners may include hydroxypropyl methylcellulose, hydroxyethyl cellulose, sodium carboxymethyl cellulose, xanthan gum, tragacanth gum, karaya gum, arabic gum, Irish moss, starch, alginates and carrageenans.

Water is a further component of the premix phase and finished product. Concentrations for either of the aforementioned may range from 1 to 50%, preferably from 5 to 30% by weight.

Copper compounds suitable for the present invention are those which will supply copper ions and are toxicologically harmless, compatible with mucous membranes and, to some extent, water-soluble. Examples of suitable copper compounds are copper sulphate, copper halides and pseudohalides (such as copper chloride), copper nitrate, copper salts of carboxylic acids in the homologous series formic acid to decanoic acid, copper salts of polybasic acids in the series oxalic acid to suberic acid, and copper salts of hydroxycarboxylic acids, including glycolic, lactic, tartaric, malic and citric acids.

Further, specific examples include copper benzoate, copper gluconate, copper phytate, copper glycerophosphate, copper propionate, and copper salicylate.

The amount of copper, calculated as the metal, which may be included in both premix and finished compositions according to the present invention, ranges from about 1 ppm to 2000 ppm, preferably 100 to 300 ppm, more preferably 150 ppm to 250 ppm. On an overall weight basis, the copper compound may range in amount from 0.01 to 5%, preferably from 0.1 to 1.0%.

Bicarbonate salts of the present invention will normally be salts of an alkali metal, such as sodium or potassium. Advantageously, the bicarbonate is included in the composition in an amount sufficient to provide a neutral and basic pH when the composition is contacted with water, preferably a pH from about 7.0 to 9.5, most preferably about 8.0 to 9.0. Typically, the concentration will range from about 0.5 to about 80%, preferably from about 5 to 50%, optimally between about 8 and 20% by weight of the total finished toothpaste.

According to the process of the invention, a reactor is charged with effective amounts of a polyol, a thickening agent, a copper compound and water. These components are blended together at a temperature no higher than about 110° F., preferably no higher than 100° F., optimally between 80° and 90° F. The lower temperature range is desirable because addition of sodium bicarbonate to the premix often causes an exotherm that can raise the temperature 10° to 15° F. Heating and blending are continued until all bacterial action has been reduced to a pharmaceutically acceptable level. The pH is then adjusted to approximately 10. Temperature is maintained at above 80° F. but below 110° F. Once all the premix components have been blended, the bicarbonate and other abrasives are added to the premix phase. Thereafter, further components, such as surfactant, flavor and colorant may be incorporated.

Surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

Additional abrasives may be selected from water-insoluble alkali or alkaline earth metal salts of metaphosphate, carbonate, aluminate and silicate. Especially preferred are silica, dicalcium phosphate and calcium carbonate. Amounts of the abrasive will range from about 5 to about 80% by weight.

Tartar control agents may be incorporated into compositions of this invention. Especially effective will be agents containing phosphorous. Inorganic phosphorous tartar control agents may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as tarter control agents include polyphosphonates such as disodium ethane-1-hydroxy-1, 1-diphosphonate (EHDP), methanediphosphonic acid, and 2-phosphonobutane-1,2,4-tricarboxylic acid.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from 0.1 to 5% by weight.

Sweetening agents such as saccharin, sodium cyclamate, aspartame, sucrose and the like may be included at levels from about 0.1 to 5% by weight.

Other additives may also be incorporated into the oral compositions including preservatives, silicones, other synthetic or natural polymers such as Gantrez S-97 ®, and anti-gingivitis actives.

The following examples will more fully illustrate the embodiments of this invention. All parts, percentages and proportions referred to herein and in the appended claims are by weight of the total composition unless otherwise stated.

EXAMPLE 1

A typical formulation of the present invention is a toothpaste whose composition is outlined in the table below:

TABLE

| Ingredient | Wt. % |
| --- | --- |
| PREMIX PHASE | |
| Polyol II (sorbitol and other sugars) | 38.1140 |
| Deionized water "A" | 4.0000 |
| Sodium saccharin | 0.5000 |
| Sodium fluoride | 0.4600 |
| Polyethylene glycol-32 | 5.0000 |
| Carboxymethyl cellulose gum | 0.8000 |
| Deionized water "B" | 5.3080 |
| Ammonia | 1.3080 |
| Copper sulphate 5-hydrate | 0.1600 |
| BASE PASTE | |
| Sodium bicarbonate, coarse granular | 15.0000 |
| Sylox 15X (thickening silica) | 4.2500 |
| Syloid 63XX (abrasive silica) | 7.5000 |
| Titanium dioxide | 0.3000 |
| FLAVOR PACKAGE | |
| Polyol II | 9.1830 |
| Sodum lauryl sulphate | 2.9790 |
| SDA 38B alcohol | 2.8380 |
| Flavor | 1.9000 |
| Menthol | 0.6000 |
| Color | 0.0050 |
| Total | 100.7000 |

PROCESSING FOR ABOVE FORMULATION

Premix

Polyol and deionized water "A" were mixed together in a vessel to which was added sodium saccharin and sodium fluoride. The gum (CMC in this case) was dispersed in molten (160° F.) polyethylene glycol and then added to the above mixture. This was mixed for about one hour to allow the gum to hydrate. Copper sulfate was dissolved in deionized water "B" followed by the addition of ammonia solution containing 27 to 30% ammonia. Mixing continued until a uniform solution was achieved (about 30 minutes).

Premix was prepared in a separate mixer and when complete, was charged into the main vessel to produce paste base. Premix was prepared in quantities adequate for production of several base paste batches.

Base Paste

This stage was where the actual toothpaste was formed. Optimal use of this mixer increases production efficiency. This is exemplified by semi-continuous processing (as described here) where separate submixes (such as premix and flavor package) were produced in separate mixers. This reduced the main mixer's batch cycle time allowing it to be used only in the steps where it was necessary, in this case, powder incorporation.

After the premix was charged into the main mixer, the ingredients for the base paste were added in the order described above and mixed until uniform.

Flavor Package

A solution was formed of Polyol II, Sodium Lauryl Sulfate and Alcohol (in a separate mixer). This was charged into a flavor package mixer with the remaining ingredients added in the order described above. The flavor package was either added to the base paste in the main mixer or added via in-line mixing during transfer to a holding tank.

EXAMPLE 2

Microbiological Method and Results

The microbiological stability of toothpaste premix was assessed with a single insult challenge test. In this test premix was insulted with a range of organisms (including bacteria, yeast and mold), then held at various temperatures over a set period of time. The microbial content of the premix was determined initially and at appropriate times thereafter to determine microbial stability. The premix will either pass (microbially stable) or fail the test based on predetermined limits.

Microbiological challenge testing indicated that in order for the premix without copper to be held for a useful amount of time, it must be kept at temperatures greater than 110° F. As a safety margin, premixes should actually be held at temperatures in excess of 125° F. Addition of copper produced a premix with excellent microbiological stability, even though it was prepared at no higher than room temperature.

| Premix | RT | 90° F. | 100° F. | 105° F. | 110° F. |
|---|---|---|---|---|---|
| No Copper | N/T | N/T | Fail | Fail | Fail |
| With Copper | Pass | Pass | Pass | N/T | N/T |

Note: N/T = not tested

The foregoing description and Examples illustrated selected embodiments of the present invention. In light thereof, various modifications will be suggested to one skilled in the art, all of which are within the spirit and purview of this invention.

What is claimed is:

1. A processing for preparing an oral toothpaste composition comprising:
   (i) blending together a toothpaste premix phase whose components comprise:
   (a) a polyol present in an amount from about 25 to 99.9% by weight;
   (b) a thickening agent present in an amount from about 0.1 to 10% by weight;
   (c) a copper compound present in an amount to provide from about 1 to about 2000 ppm copper calculated as copper metal; and
   (d) the balance water;
   (ii) maintaining said toothpaste premix phase at a temperature no higher than about 100° F. for a time sufficient to destroy bacteria in said toothpaste premix phase; and
   (iii) combining from about 0.5 to about 80% by weight of a bicarbonate salt with said toothpaste premix phase.

2. A process according to claim 1, wherein the premix phase is maintained between 80° and 100° F. during step (ii).

3. A process according to claim 1, wherein the amount of bicarbonate ranges from 8 to 20% by weight.

4. A process according to claim 1, wherein the bicarbonate salt is selected from the group consisting of sodium bicarbonate, potassium bicarbonate and mixtures thereof.

5. A process according to claim 1, wherein the copper compound is selected from the group consisting of copper sulphate, copper chloride and copper bromide.

6. An oral toothpaste composition comprising:
   (a) a polyol present in an amount from about 25 to 99.9% by weight;
   (b) a thickening agent present in an amount from about 0.1 to 10% by weight;
   (c) a copper compound present in an amount to provide from about 1 to about 2000 ppm copper calculated as copper metal;
   (d) from about 0.5 to about 80% by weight of a bicarbonate salt; and
   (e) the balance water.

7. An oral composition according to claim 6, wherein the amount of bicarbonate ranges from 8 to 20% by weight.

8. An oral composition to claim 6, wherein the bicarbonate salt is selected from the group consisting of sodium bicarbonate, potassium bicarbonate and mixtures thereof.

9. An oral composition according to claim 6, wherein the copper compound is selected from the group consisting of copper sulphate, copper chloride and copper bromide.

* * * * *